United States Patent [19]

Allen et al.

[11] Patent Number: 5,322,063
[45] Date of Patent: Jun. 21, 1994

[54] HYDROPHILIC POLYURETHANE MEMBRANES FOR ELECTROCHEMICAL GLUCOSE SENSORS

[75] Inventors: Douglas J. Allen; Kirk W. Johnson; Robert S. Nevin, all of Indianapolis, Ind.

[73] Assignee: Eli Lilly and Company, Indianapolis, Ind.

[21] Appl. No.: 771,658

[22] Filed: Oct. 4, 1991

[51] Int. Cl.$^5$ ............................................. A61B 5/05
[52] U.S. Cl. ............................ 128/635; 128/634; 204/403; 204/412; 436/817
[58] Field of Search .................. 204/403, 412, 415; 128/634, 635; 436/817

[56] References Cited

U.S. PATENT DOCUMENTS

| | | | |
|---|---|---|---|
| 4,484,987 | 11/1984 | Gough | 204/403 |
| 4,759,828 | 7/1988 | Young et al. | 204/403 |
| 4,816,130 | 3/1989 | Karakelle et al. | 128/634 |
| 4,890,620 | 1/1990 | Gough | 204/403 |
| 4,909,908 | 3/1990 | Ross et al. | 204/403 |

*Primary Examiner*—Paul Prebilic
*Attorney, Agent, or Firm*—Woodward, Emhardt, Naughton, Moriarty & McNett

[57] ABSTRACT

Homogeneous membranes permeable to oxygen and glucose composed of hydrophilic polyurethanes that are capable of absorbing from 10 to 50% of their dry weight of water. Variations in the composition of the hydrophilic polyurethanes make possible the fabrication of membranes in which the ratios of the diffusion coefficients of oxygen to glucose can be varied over a wide range. These membranes can be used in the fabrication of an electrochemical glucose sensor intended for use in vivo as an aid in the treatment of diabetes mellitus.

15 Claims, 1 Drawing Sheet

HYDROPHILIC POLYURETHANE MEMBRANES FOR ELECTROCHEMICAL GLUCOSE SENSORS

This invention relates to homogeneous membranes composed of hydrophilic polyurethanes that are useful in the fabrication of electrochemical glucose sensors, particularly those intended for in vivo use.

BACKGROUND OF THE INVENTION

At the present time, there are a number of devices commercially available that allow for external monitoring of glucose levels of urine and blood. These devices, however, do not allow for continuous monitoring, and they require a high degree of patient compliance in order to be effective.

Much research has been directed toward the development of a glucose sensor that would function in vivo as an aid, for example, in the treatment of diabetes mellitus. An implantable glucose sensor that would continuously monitor a patient's blood glucose level could serve as a hypo- and hyperglycemia alarm, and would provide physicians with more accurate information in order to develop optimal therapy. In addition, such a sensor would make possible the development of a "closed loop" insulin delivery system in which a pump delivers insulin as needed, rather than on a programmed basis.

Implantable glucose sensors have been developed based on both optical and electrochemical principles. Schultz and Mansouri have disclosed one version of an optical sensor (J. S. Schultz and S. Mansouri, "Optical Fiber Affinity Sensors," *Methods in Enzymology*, K. Mosbach, Ed., Academic Press, New York, 1988, vol. 137, pp. 349-366). An impediment to the commercial development of an optical sensor of the type disclosed by Schultz and Mansouri has been the difficulty of producing such devices on a commercial basis.

Electrochemical glucose sensors, on the other hand, can be produced using techniques common in the semiconductor industry. The ability to mass produce electrochemical glucose sensors using known commercial techniques gives them a cost advantage over optical sensors. As a consequence, considerable research has been directed toward the development of an in vivo electrochemical glucose sensor. An excellent summary of the issues relating to the development of implantable electrochemical glucose sensors has been published by Turner and Pickup (A. P. F. Turner and J. C. Pickup, "Diabetes Mellitus: Biosensors for Research and Management," *Biosensors*, 1, 85-115 (1985)).

The most favored configuration to date for an electrochemical glucose sensor involves the use of one or two enzymes to catalyze the reaction between glucose and another molecule in order to generate an electrical signal. Typically glucose oxidase is used to catalyze the reaction between glucose and oxygen to yield gluconic acid and hydrogen peroxide, as follows:

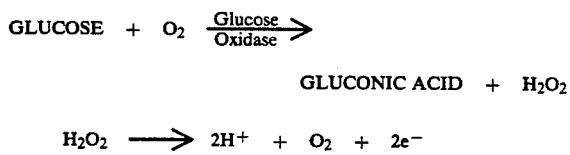

$$\text{GLUCOSE} + O_2 \xrightarrow{\text{Glucose Oxidase}} \text{GLUCONIC ACID} + H_2O_2$$

$$H_2O_2 \longrightarrow 2H^+ + O_2 + 2e^-$$

The hydrogen peroxide generated may be detected directly or it may be decomposed by a second enzyme, catalase, in which case the sensor will measure oxygen consumption by the reaction involving glucose oxidase.

The presence of an excess of molecular oxygen, relative to molecular glucose, is necessary for the operation of a glucose oxidase based glucose sensor. This presents a problem in the design of such sensors, since the concentration of oxygen in the subcutaneous tissue is much less than that of glucose. As a consequence, oxygen can become a limiting reactant, giving rise to an "oxygen deficit" problem. Some provision should therefore be made to allow operation of the sensor in an environment with an excess of oxygen.

Many attempts have been made to utilize membranes of various types in an effort to ratio the diffusion of oxygen and glucose to the sensing elements of glucose oxidase based glucose sensors to address the "oxygen deficit" problem. The simplest approach to controlling diffusion has been to use a macroporous or a microporous membrane. For example, in U.S. Pat. No. 4,759,828, Young et al. disclose the use of a laminated membrane with an outer microporous membrane having a pore size of 10 to 125A to limit the diffusion of glucose molecules. One immediate problem with macroporous or microporous membranes, however, is that the sensing element of the sensor is exposed to the environment of the body and is therefore subject to fouling. Young et al. attempted to obviate this problem by the use of a second inner membrane to exclude passage of fouling substances to the sensing element. This design creates additional problems in that transport to the sensing element through the second membrane must not be hindered. Also, because two membranes are necessary, each membrane must be extremely thin so that measurement times are not unduly long.

Another approach has been to utilize a membrane element that contains discrete hydrophilic and hydrophobic domains. In U.S. Pat. No. 4,484,987, Gough discloses a composite membrane in which an immiscible hydrophilic material is physically incorporated in a hydrophobic matrix. The purpose of such a membrane is to achieve a favorable balance between oxygen diffusion through the hydrophobic and hydrophilic matrices and glucose diffusion only through the hydrophilic domains. The effectiveness of such a membrane depends upon the relative amounts of the hydrophilic domains within the hydrophobic matrix. Such membranes are difficult to fabricate reproducibly, particularly on the scale of a glucose sensor meant for implantation within the body. Also, because of the discontinuous nature of the membranes disclosed in Gough '987, physical properties are compromised.

In U.S. Pat. No. 4,890,620, Gough discloses a further elaboration of this concept, utilizing a "two-dimensional" sensing electrode. Here the "membrane" element is physically constructed so that oxygen and glucose diffuse to the sensing electrode at right angles to one another, one direction favoring oxygen diffusion and the other favoring glucose diffusion. While a glucose sensor incorporating the diffusion element of Gough '620 may be useful for research purposes, it would be difficult to fabricate on a commercial scale because of its complexity. Additionally, constraints would be placed upon the size and configuration of the sensor in order to allow for diffusion to the sensing electrode from two directions.

Gernet et al. and Shichiri have recognized the abovementioned difficulties and have utilized a single homogeneous membrane composed of a hydrophobic polyurethane (S. Gernet, et al., "Fabrication and Characterization of a Planar Electrochemical Cell and its Application as a Glucose Sensor," *Sensors and Actuators.* 18, 59–70 (1989); M. Shichiri, "Glycaemic Control in Pancreatectomized Dogs With a Wearable Artificial Endocrine Pancreas," *Diabetologia,* 24, 179–184 (1983)). While a homogeneous hydrophobic membrane eliminates many of the difficulties mentioned above, it does not provide an optimum balance between oxygen and glucose transport to an electrochemical glucose sensor, nor is it possible to tailor the properties of the homogeneous hydrophobic polyurethane membrane utilized by Gernet et al. and Shichiri to match the design requirements of electrochemical glucose sensors.

SUMMARY OF THE INVENTION

The primary requirement for an electrochemical glucose sensor intended for in vivo use is that the supply of oxygen in the vicinity of the sensing element not be depleted. This does not mean that an electrochemical glucose sensor membrane need have an extremely high permeability to oxygen. What is needed is a membrane that can moderate the diffusion of oxygen and glucose so that the local concentration of oxygen is not depleted. It is sufficient if the ratio of the diffusion coefficient of oxygen to that of glucose is appropriate to the design of the glucose sensor.

Electrochemical glucose sensors intended for in vivo use must also be rendered biocompatible with the body, and they must be able to function in a hostile environment. The enzyme(s) used in such sensors must be protected from degradation or denaturation. At the same time, the sensing elements of such sensors must be protected from molecules which would foul the sensors or their accuracy will decrease over time.

The membranes of the present invention possess unique attributes that satisfy the above objectives. Their properties can be varied to tailor their glucose and oxygen transport behavior to match the requirements of a particular configuration of an electrochemical glucose sensor. The membranes of the present invention are particularly useful in the construction of electrochemical glucose sensors intended for in vivo use.

The homogeneous membranes of the invention are prepared from biologically acceptable polymers whose hydrophobic/hydrophilic balance can be varied over a wide range to control the ratio of the diffusion coefficient of oxygen to that of glucose, and to match this ratio to the design requirements of electrochemical glucose sensors intended for in vivo use.

The membranes of the invention are fabricated from polymers prepared by the reaction of a diisocyanate, a poly(ethylene oxide), and an aliphatic diol. The polymerization reaction may be carried out in solution or in bulk. The preferred hydrophilic polyurethanes so produced are capable of absorbing from about 10 to about 50% of their weight of water, with those capable of absorbing from about 20% to about 30% of their weight of water being preferred. By appropriate selection of the reaction components, membranes can be made from these preferred polymers that exhibit ratios of the diffusion coefficients of oxygen to glucose of up to about 4000, with ratios of about 2000 to about 4000 being preferred.

Since these polymers do not have to be crosslinked in order to develop optimum properties, they are soluble in a variety of solvents and solvent combinations, and thus can be readily fabricated into membranes of various shapes. The membranes of the invention show good adhesion to substrates in an aqueous environment and possess excellent wet-strength. A further advantage of the polymers from which the membranes of the invention are fabricated is that they possess excellent compatibility with the body, a key requirement for an implantable sensor of any type.

It is an objective of the present invention to provide hydrophilic polyurethane membranes for electrochemical glucose sensors to enhance the sensor's biocompatibility and to render the sensor insensitive to changes in the oxygen levels of subcutaneous fluids.

Further and related objects and advantages of the present invention will be apparent from the following description.

DESCRIPTION OF THE PREFERRED EMBODIMENTS

Figure 1:
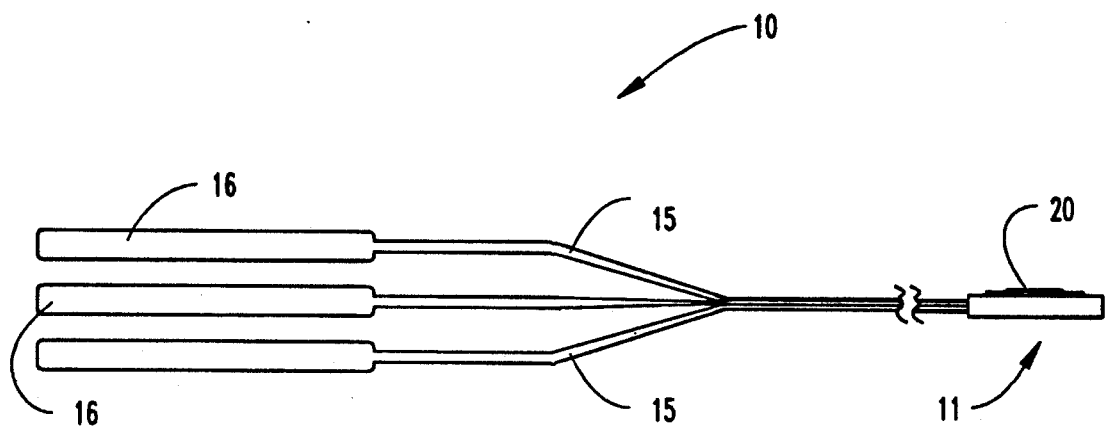
FIG. 1 is a schematic view of a glucose sensor having sensor elements with a hydrophilic polyurethane membrane of the present invention secured thereover.
Figure 2:
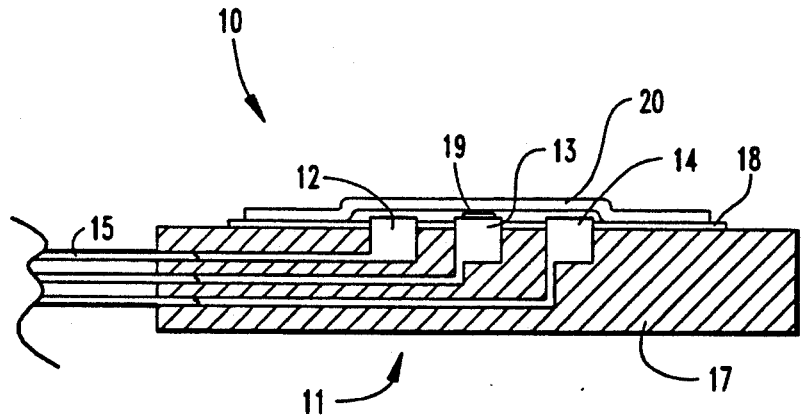
FIG. 2 shows in schematic form an implantable portion of a glucose sensor, with the sensing elements covered with a hydrophilic polyurethane membrane of the present invention.

For the purposes of promoting an understanding of the principles of the invention, reference will now be made to the preferred embodiments and specific language will be used to describe the same. It will nevertheless be understood that no limitation of the scope of the invention is thereby intended, such alterations and further modifications in the preferred embodiments, and such further applications of the principles of the invention as illustrated thereby being contemplated as would normally occur to one skilled in the art to which the invention relates.

The present invention provides a novel polyurethane membrane for use in covering or encapsulating a glucose sensor, particularly one intended for in vivo use. It has been discovered that the use of such a membrane provides many advantages including control of the glucose and oxygen reactants to permit accurate analysis, protection of the sensor from the hostile in vivo environment, and biocompatibility.

Referring to the drawings, there is shown in schematic form a glucose sensor 10 of typical construction covered or encapsulated with a membrane fabricated in accordance with the present invention. The specific construction and operation of the sensor 10 do not form a part of the present invention. For example, glucose sensors that utilize glucose oxidase to effect a reaction of glucose and oxygen are known in the art, and are within the skill in the art to fabricate. The present invention depends not on the configuration of the sensor, but rather on the use of a hydrophilic polyurethane membrane to cover or encapsulate the sensor elements. Therefore, only a brief description of an exemplary sensor is given herein. Other sensors for monitoring glucose concentration of diabetics are described, for example, in Shichiri, M., Yamasaki, Y., Nao, K., Sekiya, M., Ueda, N.: "In Vivo Characteristics of Needle-Type Glucose Sensor—Measurements of Subcutaneous Glucose Concentrations in Human Volunteers"—Horm. Metab. Res., Suppl. Ser. 20:17–20, 1988; Bruckel, J., Kerner, W., Zier, H., Steinbach, G., Pfeiffer, E.: "In Vivo Measurement of Subcutaneous Glucose Concentrations with an Enzymatic Glucose Sensor and a Wick Method," Klin. Wochenschr. 67:491-495, 1989; and Pickup, J., Shaw, G., Claremont, D.: "In Vivo Molecular Sensing in Diabetes Mellitus: An Implantable Glucose Sensor with Direct Electron Transfer," Diabetologia. 32:213-217, 1989.

Sensor 10 includes a distal portion 11 in which are located sensor elements 12-14 which are connected through leads 15 to contacts 16. Typical sensing elements would be a counter electrode 12, working electrode 13 and reference electrode 14. Contacts 16 are connected with a suitable monitoring device (not shown), which receives signals and translates this information into a determination of the glucose level detected.

In this type of sensor, glucose oxidase is also provided in the area adjacent the sensor elements, and catalyzes the reaction of glucose and oxygen. This, or a subsequent reaction, is monitored by the sensing elements, and a determination of glucose present in the surrounding subcutaneous tissue may thereby be obtained.

In one design, the sensor 10 includes a substrate material 17 comprising an electrical insulator. This substrate is preferably flexible to facilitate patient comfort. The counter, working and reference electrodes 12-14 are positioned on the substrate and isolated from one another by an insulation layer 18 patterned to selectively expose the active regions of the three electrodes. Glucose oxidase 19 is deposited on the working electrode and all three sensor/electrodes are then covered with a membrane 20 of the present invention.

The distal portion of the sensor is implanted subcutaneously into the body, and the proximal portion including contacts 16 remains external of the body. In accordance with the present invention, the implanted sensor elements 12-14 are covered with a membrane 20 of the present invention, which controls the rate of diffusion of glucose and oxygen from the surrounding body tissue to the area of the sensor elements. Membrane 20 may fully encapsulate the entire distal portion of the sensor or may simply be layered over the sensor elements. The latter approach may be preferable from the standpoint of ease of fabrication.

The membrane of the invention is formed from a hydrophilic polyurethane. Polyurethane is a thermoplastic polymer produced by the condensation reaction of a polyisocyanate and a hydroxyl-containing material. The membrane is characterized by absorbing from about 10% to about 50%, and preferably from about 20% to about 30%, of its weight in water. Also, the membrane's diffusion coefficient for oxygen should be up to about 4000 times the membrane s diffusion coefficient for glucose, and more preferably between about 2000 and about 4000. Within these preferred ranges, a person skilled in the art can synthesize a variety of suitable polyurethane compositions and readily determine the usefulness of such in the formation of membranes of the present invention.

The preferred membranes of the invention were prepared by the reaction of a diisocyanate with a poly(ethylene oxide) and an aliphatic diol. Preferred diisocyanates include aliphatic diisocyanates containing from 4 to 8 methylene units. In particular, hexamethylene-1,6-diisocyanate has been the most preferred aliphatic diisocyanate in work completed to date. Diisocyanates containing cycloaliphatic moities, such as isophorone diisocyanate and dicyclohexylmethane-4,4'-diisocyanate, may also be used with the latter being the most preferred cycloaliphatic diisocyanate. Aromatic diisocyanates may also be used, but they are less suitable for a medical application because of their extreme toxicity.

The diol component of the polymerization mixture includes a poly(ethylene oxide) and an aliphatic diol. The poly(ethylene oxide) may have an average molecular weight of from 200 to 3000 with a preferred molecular weight range of 600 to 1500, and preferably constitutes about 10 to 50 mole % of the total diol component of the polymerization mixture. Suitable aliphatic diols include ethylene glycol, diethylene glycol, 1,2-propanediol, 1,3-propanediol, and 1,4-butanediol. As will be appreciated by those skilled in the art, other aliphatic diols may be used. These preferred aliphatic diols are chosen for reasons of cost, commercial availability, solubility, reactivity, or ease of purification. The aliphatic diol preferably constitutes about 50 to 90 mole % of the total diol component of the polymerization mixture.

Polymerization was carried out using equimolar quantities of total diol and the diisocyanate. Since the poly(ethylene oxide) is hydrophilic, and the aliphatic diol is hydrophobic, variation in the molar ratio of the two will allow for the preparation of polymers with varying hydrophilic/hydrophobic balances. By a suitable choice of the molar amount and the molecular weight of the poly(ethylene oxide) and the molar amount and specific aliphatic diol, polymers can be prepared that vary from being slightly hydrophilic to very hydrophilic and which can be tailored to have ratios of the diffusion coefficient of oxygen to that of glucose of up to 4000, with ratios of about 2000 to about 4000 being preferred. Polymers having ratios of the diffusion coefficient of oxygen to glucose greater than about 4000 may be too impermeable to glucose and provide too slow a response time. Those membranes with ratios less than about 2000 may result in oxygen deficiency for electrochemical glucose oxidase based sensors.

Polymerization may be carried out in bulk or in a solvent system. Although polymerization may be carried out without a catalyst, the addition of a suitable organometallic compound such as dibutylin bis(2-ethylhexanoate) has been preferred. Bulk polymerization was typically carried out at an initial temperature of about 25° C., typically 50° C., in order to insure adequate mixing of the reactants. Upon mixing of the reactants, an exotherm was typically observed, with the temperature rising to approximately 100° C. After this initial exotherm, the reaction flask was heated at from 75° to 125° C., with 90° to 100° C. being a preferred temperature range. Heating was usually carried out for one to two hours. Solution polymerizations were carried out in a similar manner. Suitable polymerization solvents have been dimethylformamide, dimethyl sulfoxide, dimethylacetamide, halogenated solvents such as 1,2,3-trichloropropane, and ketones such as 4-methyl-2-pentanone. Dimethylformamide has been a preferred solvent. When polymerization was carried out in a solvent, heating of the reaction mixture was typically carried out for three to four hours.

Polymers prepared by bulk polymerization were dissolved in dimethylformamide and precipitated from water. Polymers prepared in solvents that are not miscible with water were isolated by vacuum stripping of the solvent. These polymers were then dissolved in dimethylformamide and precipitated from water. After thoroughly washing with water, polymers were dried in vacuo at 50° C. to constant weight.

EXAMPLE I

Typical Procedure for Bulk Polymerization 4.80 g. of poly(ethylene oxide) of molecular weight 600, 2.50 g. of ethylene glycol, and 8.07 g. of hexamethylene-1,6-diisocyanate were charged to a 100 ml. flask. The flask was continually purged with nitrogen. The reaction mixture was heated to 50° C., and then 10 mg. of dibutylin bis(2-ethylhexanoate) dissolved in 7 ml. of 4-methyl-2-pentanone were added to the reaction mixture. The reaction quickly became exothermic, with the temperature rising to 100° C. within a few minutes. The reaction mixture was allowed to cool to 90° C., and it was heated at this temperature for 60 minutes. During this time the reaction mixture changed from a clear viscous liquid to a translucent solid. The polymer was removed from the flask by dissolution in 200 ml. dimethylformamide (90° C.). After cooling to room temperature, the polymer solution was poured into 2 liters of deionized water with vigorous stirring. The precipitated polymer was torn into small pieces and soaked in deionized water for 24 hours, with frequent changes of water. The polymer (number 1 in the Tables) was dried in a vacuum oven at 50° C. to constant weight.

EXAMPLE II

Typical Procedure for Solution Polymerization 14.40 g. of poly(ethylene oxide) (PEO) of molecular weight 600, 12.73 g. of diethylene glycol, 24.22 g. of hexamethylene-1,6-diisocyanate, and 250 ml. of dimethylformamide were added to a 1000 ml. flask. The flask was continually purged with nitrogen. The reaction mixture was heated to 50° C., and 30 mg. of dibutylin bis-(2-ethylhexanoate) dissolved in 25 ml. of 4-methyl-2-pentanone were added to the flask. A slight exotherm caused the temperature to rise to approximately 55° C. The reaction mixture was then heated at 75° C. for 120 minutes and then at 90° C. for another 120 minutes. There was a noticeable increase in viscosity of the reaction mixture during this time. The reaction mixture was diluted with 100 ml. of dimethylformamide and was allowed to cool to room temperature. The solution was poured into 5 liters of vigorously stirred water. The precipitated polymer (number 2 in the Tables) was isolated as in Example I.

Membranes were prepared by casting films from a suitable solvent onto glass using a Gardner knife (Gardner Labs). The solvent chosen will depend on the particular chemical structure of the polymer. Chloroform has been the preferred solvent in work completed to date, since it is readily volatile. Not all polymers of the invention, however, are soluble in this solvent, in which case dimethylformamide has been the preferred solvent. After removal of the solvent, the membranes were hydrated with deionized water for 30–60 minutes. They were then removed and transferred to a Mylar® support sheet. Wet film thicknesses were measured with a micrometer before removal from the support.

Diffusion constants were measured in a standard permeability cell (Crown Glass Co., Inc.) maintained at 37.0° C., plus or minus 0.1° C., using Fick's relationship:

$$J = -D \, dC/dx$$

where J is total flux, D is the diffusion constant, and dC/dx is the concentration gradient across the membrane.

Oxygen diffusion constants were determined by securing the membrane with two rubber gaskets between the two halves of a diffusion cell maintained at 37.0° C., plus or minus 0.1° C., and clamping the two halves together. Each side of the cell was filled with phosphate buffered saline. One side was saturated with nitrogen while the other side was saturated with air. A calibrated oxygen sensor (Microelectrodes, Inc.) was placed in the nitrogen side of the cell, and measurements were taken at 5 minute intervals until the system reached equilibrium.

Glucose diffusion constants were determined as above except that one half of the cell was filled with phosphate buffered saline containing 300 mg/dl of glucose. The concentration of glucose in each half of the cell was measured at appropriate intervals using a Cooper Assist Clinical Analyzer.

Water pickup was determined on films 4.5 cm. in diameter and less than 0.5 mm. thick at room temperature. After evaporation of the casting solvent, films were dried to constant weight at 50° C. in vacuo. weighed, immersed in deionized water for 24 hours, removed and blotted with filter paper, and weighed. Percent water pickup was determined from the formula $$\% \text{ Pickup} = (W_w - W_d)/W_d \times 100$$

where $W_w$ is the weight of the swollen film and $W_d$ is the weight of the dry film.

In accordance with the polymerization reactions of Examples I and II, polymers and resulting membranes may be readily prepared having a wide range of oxygen and glucose diffusion constants and of water pickup. Exemplary compositions were prepared as described in the foregoing Examples, and are identified by composition and % water pickup in Table I. Oxygen and glucose diffusion coefficients, and the ratio of the diffusion coefficient of oxygen to that of glucose, for the resulting membranes are listed in Table II. These formulations demonstrate the ability to vary these parameters over the desired ranges previously described. This control enables one in the art to tailor the membranes to particular glucose sensors.

TABLE I

| Polymer | Diisocyanate(M) | Glycol(M) | PEO(M) | Type | % Water Pickup |
|---|---|---|---|---|---|
| 1 | HMDI (0.048) | Ethylene (0.040) | 600(0.008) | Bulk | 22.0 |
| 2 | HMDI (0.048) | Diethylene (0.040) | 600(0.008) | DMF | 24.5 |
| 3 | HMDI (0.048) | Diethylene (0.040) | 1500(0.008) | Bulk | 56.0 |
| 4 | HMDI (0.054) | Diethylene (0.048) | 1000(0.006) | Bulk | 21.8 |
| 5 | HMDI (0.052) | Diethylene (0.048) | 600(0.004) | Bulk | 9.4 |
| 6 | HMDI (0.052) | Diethylene (0.048) | 1000(0.004) | Bulk | 15.0 |
| 7 | MCHI (0.045) | Diethylene (0.042) | 1500(0.003) | Bulk | 13.4 |
| 8 | HMDI (0.048) | Diethylene (0.042) | 600(0.006) | Bulk | 20.0 |

HMDI = Hexamethylene-1,6-diisocyanate
MCHI = Dicyclohexylmethane-4,4'-diisocyanate

TABLE II

| Polymer | D (cm²/sec) Oxygen | D (cm²/sec) Glucose | Ratio DOxygen/DGlucose |
|---|---|---|---|
| 1 | $5.50 \times 10^{-6}$ | $17.4 \times 10^{-8}$ | 32 |
| 2 | $8.83 \times 10^{-6}$ | $2.33 \times 10^{-9}$ | 3790 |
| 3 | $6.93 \times 10^{-6}$ | $7.60 \times 10^{-8}$ | 20 |
| 4 | $4.59 \times 10^{-6}$ | $1.81 \times 10^{-8}$ | 254 |
| 5 | $3.87 \times 10^{-6}$ | * | — |
| 6 | $5.72 \times 10^{-6}$ | $3.85 \times 10^{-8}$ | 149 |
| 7 | $4.83 \times 10^{-6}$ | $4.78 \times 10^{-8}$ | 101 |
| 8 | $1.6 \times 10^{-5}$ | $1.1 \times 10^{-8}$ | 1454 |

* = Impermeable

The preferred membrane identified as Polymer 2 in Tables I and II was evaluated in vitro and in vivo with an amperometric platinum-silver/silver chloride glucose sensor. Information concerning the construction of this sensor has been previously published, R. J. Morff, D. Lipson, K. W. Johnson, J. J. Mastrototaro, C. C. Andrew, A. R. Potvin, "Reproducible Microfabrication of Electroenzymatic Glucose Sensors on a Flexible Substrate," *Proc. 1st World Congress on Biosensors*, (May 2–4, 1990); J. J. Mastrototaro, K. W. Johnson, R. J. Morff, D. Lipson, C. C. Andrew, "An Electroenzymatic Glucose Sensor Fabricated on a Flexible Substrate," *Proc. Third International Meeting on Chemical Sensors*, (Sep. 24–26, 1990), and the disclosures of these publications concerning this sensor are incorporated herein by reference.

The operation of this sensor is based on the reaction of glucose with oxygen in the presence of glucose oxidase to generate hydrogen peroxide. The hydrogen peroxide is subsequently oxidized at the platinum anode, resulting in the generation of a signal that is proportional to glucose concentration.

The membrane was applied over the sensing region. The following in vitro and in vivo evaluations of the coated sensor were then conducted.

In the in vitro testing, a potential of +0.6 V vs. Ag-/AgCl was applied to the working electrode to oxidize the hydrogen peroxide produced by the reaction of glucose and oxygen in the presence of glucose oxidase. The current produced by this reaction was linearly correlated to the amount of glucose present in a test solution.

In order to fully characterize the performance of a glucose sensor designed for implantation in subcutaneous tissue, it was necessary to test not only the sensor's response to changes in the concentration of glucose, but also to changes in the concentration of oxygen. A computer-controlled system was built to automatically expose sixteen sensors provided with membranes of the invention simultaneously to an array of four different glucose concentrations: 0, 100, 200, and 400 mg/dL and four different oxygen concentrations: 1, 2, 5, and 20.9% oxygen (approximately 7–150 mmHg).

Using this system, it was found that the sensors encapsulated in the membrane responded linearly to glucose concentrations ranging from 0–400 mg/dL (correlation coefficient >0.98) and had a very reproducible baseline value in a buffer solution with no glucose. This characteristic of the sensor allowed a one-point calibration to be adequate. In addition, varying the oxygen concentration of the calibration solution between 1 and 20.9% had no effect on the output of the sensor, even at high glucose concentrations. The resolution was better than 10% throughout the entire calibration range and the 90% response time for a change in the glucose concentration from 0 to 100 mg/dL was less than 90 seconds.

A long-term evaluation was also performed whereby the sensors were continuously exposed to a glucose solution (100 mg/dL) at 37° C. for 72 hours. The current output from the sensors was stable, drifting less than 10% over the duration, which demonstrated the sensors' ability to function as continuous monitors for at least three days.

In in vivo testing completed to date, the animal model utilized for study was the New Zealand White Rabbit. The rabbit was surgically equipped with venous and arterial cannulas to allow infusion of fluids and withdrawal of arterial blood samples for analysis.

Prior to implantation in the subcutaneous tissue, the sensor encapsulated in the membrane was inserted into a polyethylene or Teflon ® cannula. Single and double lumen cannulas have been utilized successfully. Stainless steel needle stock was inserted into the cannula to provide rigidity during insertion. This stock may be left in the cannula or removed following implantation to allow more flexibility. A connector was attached to the sensor and sutured to the skin under local anesthetic.

A standard glucose tolerance test was conducted whereby a glucose bolus was given intravenously. An arterial blood presample and samples at 1, 2, 5, 10, 30, and 60 minutes following the injection were collected. This type of test was useful for determining the lag time between a glucose bolus injection into a vein and the peak glucose level in the subcutaneous tissue as indicated by the sensor. An average lag time of 10 minutes was found, which is thought to be a physiologic phenomenon related to the time required for the diffusion of glucose through the capillary wall to the subcutaneous tissue.

A more definitive test, the glucose clamp test, was also conducted. This test involved either elevating or reducing the rabbit's blood glucose level by continuously infusing glucose or insulin. The rate of change in the blood glucose level of the rabbit was slower for a glucose clamp test compared to a tolerance test, making it a test that more closely mimics actual physiologic diabetic conditions. In addition, elevated or reduced glucose levels could be maintained for the period of time necessary for the plasma and subcutaneous glucose values to reach steady-state. This allowed a direct comparison between sensor output and plasma glucose levels.

An excellent correlation between the plasma and subcutaneous tissue glucose values was established. The results from these tests indicated that the sensor provided with a membrane of the present invention will satisfactorily respond to changes in the plasma glucose concentration from as low as 40 mg/dL to in excess of 400 mg/dL, in vivo.

The membranes of the present invention are readily formulated to optimize the diffusion and water pickup characteristics for a given glucose sensor. Membranes of the present invention having water pickups of about 10%, 30% and 50% have been evaluated. In addition, the inventive membranes having oxygen to glucose diffusion ratios of about 1000, 2000 and 3000 perform acceptably in the foregoing circumstances.

While the invention has been described in the foregoing description, the same is to be considered as illustrative and not restrictive in character, it being understood that only the preferred embodiments have been described and that all changes and modifications that come within the spirit of the invention are desired to be protected.

What is claimed is:

1. A homogeneous membrane and an electrochemical glucose sensor combination, said electrochemical glucose sensor including means for evaluating the reaction of glucose and oxygen, said membrane adapted to control the diffusion of glucose and oxygen to the sensor elements, said membrane comprising a hydrophilic polyurethane composition comprising the product of the reaction mixture of:
a diisocyanate selected from the group consisting of hexamethylene-1,6-diisocyanate, dicyclohexylmethane 4,4'-diisocyanate, and isophorone diisocyanate, and constituting about 50 mole % of the reaction mixture;
a poly(ethylene oxide) having an average molecular weight of about 600 to about 1500; and
an aliphatic diol selected from the group consisting of ethylene glycol, diethylene glycol, 1,2-propanediol, 1,3-propanediol, and 1,4-butanediol,
said membrane having an equilibrium water content of about 10% to about 50% and having a ratio of its diffusion coefficient for oxygen to its diffusion coefficient for glucose of up to about 4000, the poly(ethylene oxide) and aliphatic diol components constitute a total diol content of the reaction mixture the total diol content of the reaction mixture comprising from about 10% to about 50% poly(ethylene oxide) and from about 50% to about 90% aliphatic diol.

2. The device of claim 1 wherein the aliphatic diol is diethylene glycol.

3. The device of claim 1 wherein the poly(ethylene oxide) has an average molecular weight of about 600.

4. The device of claim 1 wherein the diisocyanate is hexamethylene-1,6-diisocyanate.

5. The device of claim 4 wherein the aliphatic diol is diethylene glycol.

6. The device of claim 5 wherein the poly(ethylene oxide) has an average molecular weight of about 600.

7. An implantable device for determining the level of glucose in a body, which device comprises:
an electrochemical glucose sensor including means for evaluating the reaction of glucose and oxygen, the evaluating means including sensor elements, and
a membrane secured to said glucose sensor covering the sensor elements and adapted to control the diffusion of glucose and oxygen to the sensor elements, said membrane comprising a hydrophilic polyurethane composition comprising the product of the reaction mixture of:
a diisocyanate selected from the group consisting of hexamethylene-1,6-diisocyanate, dicyclohexylmethane 4,4'-diisocyanate, and isophorone diisocyanate, and constituting about 50 mole % of the reaction mixture;
a poly(ethylene oxide) having an average molecular weight of about 600 to about 1500; and
an aliphatic diol selected from the group consisting of ethylene glycol, diethylene glycol, 1,2-propanediol, 1,3-propanediol, and 1,4-butanediol,
said membrane having an equilibrium water content of about 10% to about 50% and having a ratio of its diffusion coefficient for oxygen to its diffusion coefficient for glucose of up to about 4000, the poly(ethylene oxide) and aliphatic diol components constitute a total diol content of the reaction mixture the total diol content of the reaction mixture comprising from about 10% to about 50% poly(ethylene oxide) and from about 50% to about 90% aliphatic diol.

8. The device of claim 7 in which the aliphatic diol is diethylene glycol.

9. The device of claim 7 in which the poly(ethylene oxide) has an average molecular weight of about 600.

10. The device of claim 8 in which the diisocyanate is hexamethylene-1,6-diisocyanate.

11. The membrane of claim 1 wherein said device has an equilibrium water content of about 20% to about 30%.

12. The membrane of claim 1 in which said device has a ratio of its diffusion coefficient for oxygen to its diffusion coefficient for glucose of about 2000 to about 4000.

13. The membrane of claim 12 wherein said device has an equilibrium water content of about 20% to about 30%.

14. The device of claim 7 wherein said membrane has an equilibrium water content of about 20% to about 30%.

15. The device of claim 7 in which said membrane has a ratio of its diffusion coefficient for oxygen to its diffusion coefficient for glucose of about 2000 to about 4000.

* * * * *